United States Patent [19]

Laue

[11] Patent Number: 4,662,220
[45] Date of Patent: May 5, 1987

[54] WATER-ABSORBING CAPACITOR SYSTEM FOR MEASURING RELATIVE HUMIDITY

[75] Inventor: Eric G. Laue, San Marino, Calif.

[73] Assignee: The United States of America as represented by the Administrator of the National Aeronautics and Space Administration, Washington, D.C.

[21] Appl. No.: 746,809

[22] Filed: Jun. 20, 1985

[51] Int. Cl.[4] ............................................. G01W 1/00
[52] U.S. Cl. ................................. 73/336.5; 324/61 R
[58] Field of Search ............... 73/336.5, 336; 340/603; 338/35; 324/61 R

[56] References Cited

U.S. PATENT DOCUMENTS

| | | | |
|---|---|---|---|
| 2,412,782 | 12/1946 | Palmer | 73/336.5 |
| 3,164,004 | 1/1965 | King, Jr. | 73/336.5 |
| 3,287,974 | 11/1966 | Clemochowski | 73/336.5 |
| 3,392,348 | 7/1968 | Horwitz | 73/336.5 |
| 3,427,864 | 2/1969 | King, Jr. | 73/29 |
| 3,523,244 | 8/1970 | Goodman et al. | 324/61 |
| 4,083,765 | 4/1978 | Lawson | 204/195 |
| 4,143,177 | 3/1979 | Kovac et al. | 427/79 |
| 4,160,374 | 7/1979 | Crump et al. | 73/76 |
| 4,161,660 | 7/1979 | Gallant | 236/44 R |
| 4,203,087 | 5/1980 | Kovac et al. | 338/35 |
| 4,242,096 | 12/1980 | Oliveira et al. | 422/61 |
| 4,317,084 | 2/1982 | Senturia et al. | 331/65 |
| 4,482,581 | 11/1984 | Lorin et al. | 427/79 |

FOREIGN PATENT DOCUMENTS

| | | | |
|---|---|---|---|
| 148945 | 9/1983 | Japan | 73/336.5 |
| 196441 | 11/1983 | Japan | 73/336.5 |
| 196442 | 11/1983 | Japan | 73/335 |
| WO/03139 | 9/1983 | PCT Int'l Appl. | 73/336.5 |
| 2111684 | 7/1983 | United Kingdom | 73/336.5 |
| 160344 | 12/1964 | U.S.S.R. | 73/336.5 |

OTHER PUBLICATIONS

R. Samuel et al., Electronic Humidity Measuring System, Patent Associated Literature, 4-1976.

*Primary Examiner*—Stewart J. Levy
*Assistant Examiner*—Hezron E. Williams
*Attorney, Agent, or Firm*—Paul F. McCaul; John R. Manning; Thomas H. Jones

[57] ABSTRACT

A method and apparatus using a known water-absorbent polymer as a capacitor which is operated at a DC voltage for measuring relative humidity. When formed as a layer between porous electrically-conductive electrodes and operated in an RC oscillator circuit, the oscillator frequency varies inversely with the partial pressure of the moisture to be measured. In a preferred embodiment, the capacitor is formed form Nafion and is operated at a low DC voltage with a resistor as an RC circuit in an RC oscillator. At the low voltage, the leakage current is proper for oscillation over a satisfactory range. The frequency of oscillation varies in an essentially linear fashion with relative humidity which is represented by the moisture being absorbed into the Nafion. The oscillation frequency is detected by a frequency detector.

3 Claims, 3 Drawing Figures

WATER-ABSORBING CAPACITOR SYSTEM FOR MEASURING RELATIVE HUMIDITY

BACKGROUND OF THE INVENTION

1. Origin of the Invention

The invention described herein was made in the performance of work under a NASA Contract and is subject to the provisions of Public Law 96-517 (35 USC 202) in which the contractor has elected not to retain title.

2. Field of the Invention

This invention relates to a new method and system for measuring relative humidity by using a known water-absorbent polymer operating as a capacitor circuit element in an RC oscillator circuit which exhibits a frequency that varies inversely with the partial pressure of the moisture vapor in an area to be measured. I have discovered that a water-absorbent polymer, when formed as a capacitor between porous electrically-conductive electrodes, will absorb moisture. The electrical properties of an RC oscillator, including the capacitor, vary linearly in frequency when compared to variations in relative humidity.

One preferred form of capacitor was subjected to a low DC voltage of about 3 to 3.2 volts. In this preferred embodiment the RC circuit element is formed from a Nafion capacitor which is operated in an RC oscillator circuit at the low DC voltage. At that low voltage the reactive current through the Nafion is sufficiently high to allow RC oscillation over a satisfactory humidity range. The frequency of oscillation varies in an essentially linear fashion with relative humidity which is represented by the moisture being absorbed into the Nafion. The range of oscillation is detected by a frequency detector. Thus, the amount of moisture varies the oscillator frequency and a simple, effective measuring system is attained.

3. Background Discussion

Nafion is water-absorbent and its use in a hygrometer as a moisture variable resistor is known in the art, as exemplified by U.S. Pat. No. 4,083,765. Various other moisture variable resistance structures using absorbent materials having a porous layer are shown in U.S. Pat. Nos. 4,143,177 and 4,203,087. A water-permeable layer in a capacitive hygrometer is disclosed in U.S. Pat. No. 4,482,581.

The inventor is aware of two prior art NASA new technology reports identified by NPO-13948 entitled "Long Lasting Solid Polymer Electrolytic Hygrometer" (Jet Propulsion Laboratory, May 1976) and NPO-15722 entitled "Trace Water Sensing in Space" (Jet Propulsion Laboratory, December 1981). These reports describe, as is well known, that typical polymer film material such as polyphosphoric acid film and sulphonated fluorocarbon polymers (DuPont Nafion) have excellent water absorption characteristics and superior chemical resistance. In these disclosures an attempt is made to read picoampere current variations as a measurement of local relative humidity. Such small currents result in an expensive and highly-sensitive system which is not only delicate but suffers from reliability, as discussed in more detail below.

The problem presented by the NASA prior art approaches is that, in both cases, the mode of water detection involves electrolysis of water absorbed on the polymer film and the presence of a chemical electrolyte. The use of high voltage in the electrolysis operation and/or the gases produced thereby tend to make the measurements unreliable. The electrodes become corroded and the corrosion also makes the measurements unreliable.

Although it has long been known as a desirable goal to monitor absorbed moisture on a polymer film by a simple, efficient nonelectrolytic system, attainment of that goal was not available until the advent of this invention.

SUMMARY OF THE INVENTION

A water-absorbent sulphonated fluorocarbon material is formed into a capacitor which is connected with a resistor into an RC oscillator circuit. This invention involves the discovery that the RC oscillator behavior varies inversely with the partial pressure of the water content, which is a function of relative humidity. Using the capacitor in an RC oscillator circuit running at a low DC voltage range of about 3 to 3.2 volts produces a variable frequency. The oscillation varies in a linear manner with relative humidity and, thus, detection of the oscillation frequency yields a simple and efficient measurement of water vapor adsorbed by the film.

In a preferred embodiment, the water-absorbing capacitor was connected in circuit with a series resistor across a low DC voltage of about 3.2 volts to form a simple RC switching oscillator having a Schmidt trigger as the switching element. A known frequency counter is used as a frequency detector to yield relative humidity measurements.

DETAILED DESCRIPTION OF THE DRAWINGS

Figure 1:
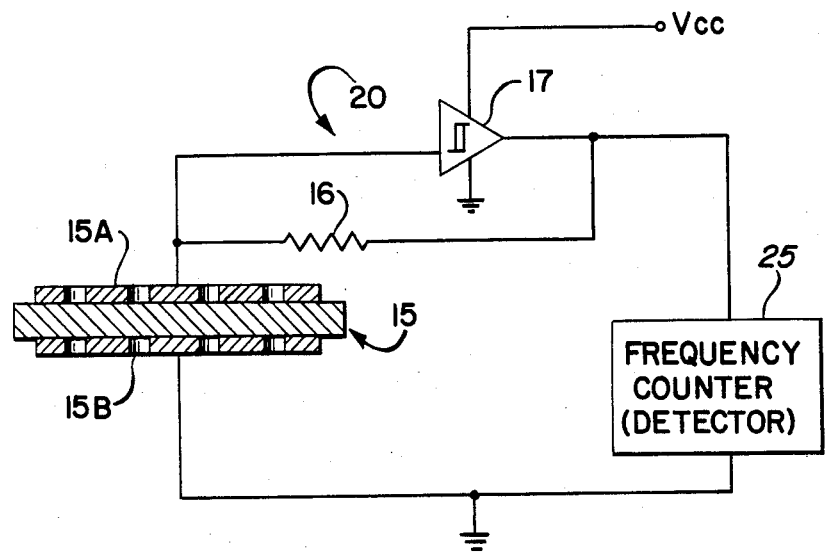
FIG. 1 is a schematic diagram of a simple RC oscillator and frequency detector in accordance with this invention.

FIG. 1 depicts the use of a water-absorbing element 15 formed from a layer of polymer film sandwiched between porous and electrically-conductive electrodes 15A and 15B. The element is used in a well-known RC oscillator circuit 20 as shown in FIG. 1.

Figure 2:
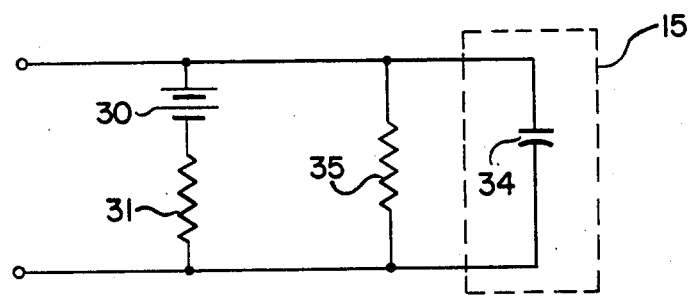
FIG. 2 depicts what is presently known to be the equivalent electrical circuit of a water-absorbent plastic film sandwiched between two porous electrically-conductive electrodes.

Reference to FIG. 2 depicts what the inventor hypothesizes is the equivalent electrical circuit for element 15. As noted in FIG. 2, there is a series connected battery 30 and resistor 31 formed in a parallel circuit with both capacitor 34 and resistor 35. Although the relative values of the equivalent circuit components are not presently known, they are not deemed significant to this application. The discovery of this invention is based upon the fact that an RC oscillator employing the circuit element 15 has a frequency which varies inversely with the partial pressure of the vapor that is absorbed by element 15.

The oscillator circuit 20 makes use of the element 15 connected in series with a resistor 16 to form an RC circuit. For simplicity, the circuit element is referred to hereinafter as a capacitor. A Schmidt trigger 17 of any well-known type such as, for example, an RCA-CD 4093 is connected between a direct current voltage $V_{cc}$ of 3 to 3.2 volts and ground. The input and output of the trigger circuit is connected in commonly-known fashion to the capacitor 15 and resistor 16 to form a known RC oscillator circuit 20. Any well-known frequency counter 25 is used to detect the frequency of oscillation and provide a suitable output signal. Either visual or electrical output signals are acceptable outputs for such a counter 25.

While an exhaustive study of the reasons why the relative humidity is linear at the low DC voltages of this invention has not yet been undertaken, certain theory is believed applicable and worthy of mention. First, a study of leakage current must be made based upon the material being used. Nafion was formed into a dual plate capacitor 15 having upper and lower plate surfaces 15A and 15B. The upper and lower Nafion surfaces were four square inches. With this capacitor 15 at a DC voltage of greater than 3.5 volts the leakage resistance, which is nonlinear with applied voltage, prevented oscillation. At 3.2 volts, however, oscillation occurred over a suitable frequency range to provide nearly linear and reliable relative humidity measurements. At the lower voltage, the frequency of the oscillator changed in direct proportion to the water content absorbed by the Nafion. It is believed that, at the lower voltage range of this invention, the water does not disassociate into its gases nor does it act as a storage battery. Instead, it serves as a simple and directly-varying capacitor which has a leakage resistance that is nonlinear over a wide range of relative humidity. At the higher voltages and higher humidity, it is believed that the known resistive property of Nafion creates too much leakage current since the water itself acts as a good electrical conductor.

Figure 3:
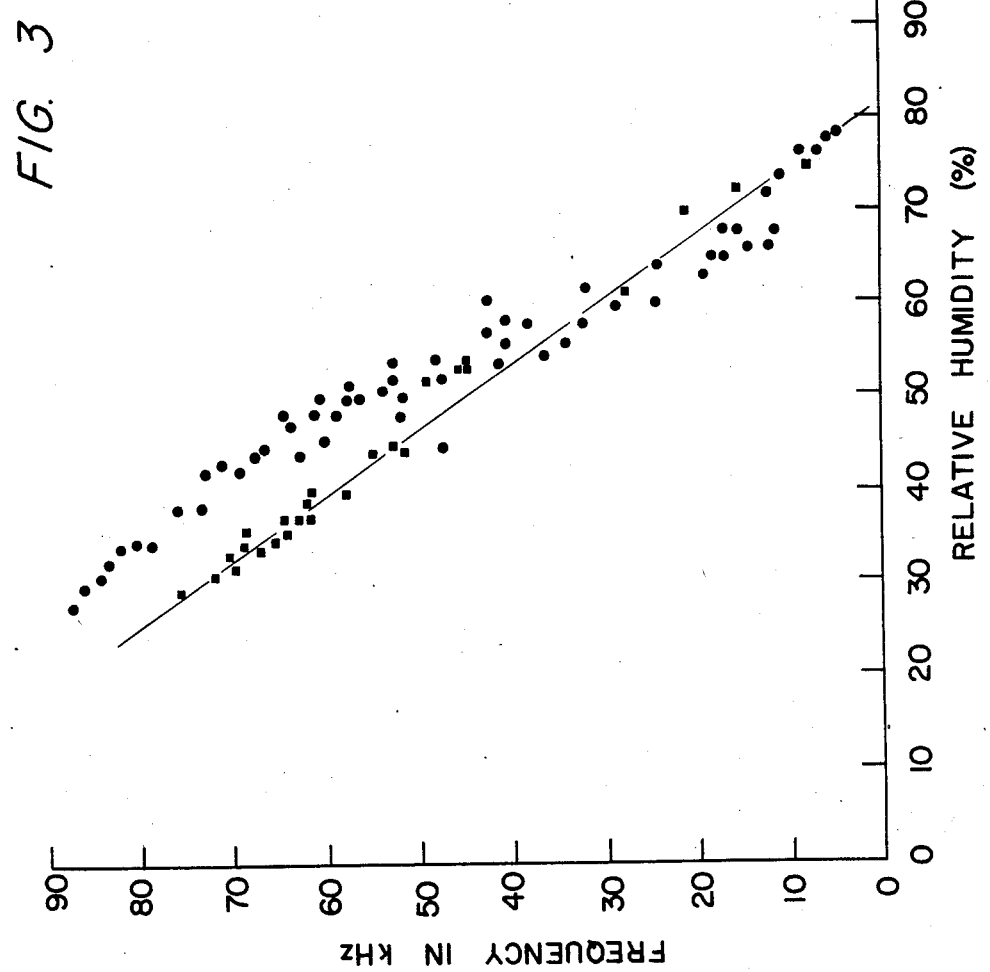
FIG. 3 depicts a nearly-linear graph of real time frequency readings in kHz and relative humidity values in percentage.

FIG. 3 represents an intercomparison of data on relative humidity from a Belfort temperature/humidity recorder, as shown by the squares. The dark colored dots represent data taken from a Honeywell relative humidity recorder. In the case of both graphs, a simultaneous frequency reading from the detector 25 of FIG. 1 was taken in real time for the two different humidity recorders. It should be noted that the swings above and below the linear dashed line were not as severe in the case of the Honeywell unit.

The intercomparison of FIG. 3 shows a nearly linear relation between the observed signal frequency read by detector 25, FIG. 1, and the relative humidity values which are scaled along the horizontal axis in FIG. 3. The data shown in FIG. 3 was obtained with the aforementioned Nafion capacitor 15 and a DC voltage of about 3.2 volts as the oscillator voltage.

While the low DC voltage of 3.0 to 3.2 volts has proven very beneficial over a wide frequency range and a wide range of relative humidity, the invention does have application at higher DC voltages. For example, in a vacuum where very minute traces of water are present, an impressed voltage of up to 15 volts has been used to achieve oscillation in an RC oscillator circuit 20. In such a vacuum, the device is sensitive and is useful over a narrowly-limited range of relative humidity. The small amount of moisture present allows the higher voltage to be employed. When more moisture is present, then the water is a good conductor and the leakage current prevents oscillation.

The output signal amplitude for the circuit of FIG. 1 is about 0.8 of the applied voltage. Such an output signal is readily readable. Use of a frequency counter 25 obviates the necessity, as in the case of the prior art, of attempting to detect very small currents. Frequency can be measured with greater accuracy and resolution than is the case with very small current levels: Finally, frequency values are easier to process by computer manipulation. In the case of the reduction to practice of this invention, the frequency counter 25 supplied a readout as a digital signal. The prior art, in contrast, provides an analog signal output.

Use of the low DC voltage makes the invention particularly attractive for measurement of the water in various locations of spacecraft, such as a shuttle bay. Other foreseen applications include remote soil and crop monitoring which may advantageously be accomplished with this invention.

The above description presents the best mode contemplated in carrying out the invention. The invention is, however, susceptible to modifications and alternate constructions from the embodiments shown in the drawings and described above. Consequently, it is not the intention to limit the invention to the particular embodiments disclosed. On the contrary, the invention is intended and shall cover all modifications, sizes and alternate constructions falling within the spirit and scope of the invention, as expressed in the appended claims when read in light of the description and drawings.

What is claimed is:

1. A system for determining relative humidity comprising:
    a circuit element functioning as a capacitor formed of sulphonated fluorocarbon material sandwiched between electrically-conductive and porous electrodes for permitting the sulphonated fluorocarbon material to absorb moisture;
    an RC switching oscillator including said circuit element as a capacitor and a resistor in an RC circuit for control of the frequency of said switching oscillator as a function of the RC time constant of said RC circuit;
    a source of DC voltage impressed across said RC circuit, said voltage being selected to be sufficiently low to not cause current to be conducted through said material; and
    means for detecting the oscillator frequency of said oscillator as a measurement of said relative humidity.

2. A device in accordance with claim 1 wherein:
    said capacitor circuit element is comprised of upper and lower electrically-conductive plates with openings therein to expose to moisture upper and lower surfaces of said sulphonated fluorocarbon material.

3. A device in accordance with claim 1 and further comprising:
    a frequency counter connected to said RC oscillator for measuring the frequency of said RC oscillator as a determination of relative humidity.

* * * * *